US007824883B2

(12) United States Patent
Powers et al.

(10) Patent No.: US 7,824,883 B2
(45) Date of Patent: *Nov. 2, 2010

(54) METHOD AND APPARATUS FOR DETECTING THE PRESENCE OF MICROBES WITH FREQUENCY MODULATED MULTI-WAVELENGTH INTRINSIC FLUORESCENCE

(76) Inventors: Linda S. Powers, 1026 Eastridge Dr., Logan, UT (US) 84321; Christopher R. Lloyd, 2574 N. 200 East, Logan, UT (US) 84341

( * ) Notice: Subject to any disclaimer, the term of this patent is extended or adjusted under 35 U.S.C. 154(b) by 642 days.

This patent is subject to a terminal disclaimer.

(21) Appl. No.: 11/827,226

(22) Filed: Jul. 10, 2007

(65) Prior Publication Data

US 2008/0032327 A1 Feb. 7, 2008

Related U.S. Application Data

(63) Continuation-in-part of application No. 10/749,329, filed on Dec. 31, 2003, now abandoned.

(51) Int. Cl.

| | |
|---|---|
| ***C12Q 1/04*** | (2006.01) |
| ***C12Q 1/00*** | (2006.01) |
| ***C12Q 1/06*** | (2006.01) |
| ***C12Q 1/16*** | (2006.01) |

(52) U.S. Cl. .............................. 435/34; 435/4; 435/35; 435/39

(58) Field of Classification Search ...................... None
See application file for complete search history.

(56) References Cited

U.S. PATENT DOCUMENTS

| | | | | |
|---|---|---|---|---|
| 6,750,006 | B2 * | 6/2004 | Powers et al. | 435/4 |
| 7,211,377 | B1 * | 5/2007 | Powers et al. | 435/4 |

* cited by examiner

*Primary Examiner*—Herbert J. Lilling
(74) *Attorney, Agent, or Firm*—K. S. Cornaby; Jones Waldo Holbrook & McDonough

(57) ABSTRACT

Method and apparatus for the detection of microbes in liquids, in air and on non-living surfaces in which samples are exposed to frequency-modulated electromagnetic radiation of specific energies capable of exciting various metabolites, cofactors and cellular and spore components, with the microbial cells to be sampled (and more specifically the excited metabolites, cofactors and/or other cellular components) contained therein emit fluorescence that can be measured that is similarly frequency-modulated provided that the excitation frequencies are longer than the fluorescence lifetime of the excited intrinsic microbial fluorophore. The contribution to the measured signal due to each excitation frequency resulting from microbial intrinsic fluorescence is determined with a method capable of calculating the intensity of each frequency-modulated signal, and the relative total fluorescent signals of the intrinsic microbial components associated with each excitation frequency are required to lie within physiological ranges, with the amplitude of the fluorescence signals used to enumerate the microbe content in the sample.

3 Claims, 4 Drawing Sheets

METHOD AND APPARATUS FOR DETECTING THE PRESENCE OF MICROBES WITH FREQUENCY MODULATED MULTI-WAVELENGTH INTRINSIC FLUORESCENCE

CROSS-REFERENCE TO RELATED APPLICATIONS

This is a CIP application of prior U.S. patent application Ser. No. 10/749,329 filed on Dec. 31, 2003 now abandoned of Linda S. Powers and Christopher R. Lloyd.

FIELD OF THE INVENTION

This invention relates to a method and apparatus for sensing the presence of microbes (bacteria, fungi, protozoa, rickettsiae and/or other microorganisms) and spores on non-living surfaces, in air and in liquids using frequency-modulated multi-wavelength intrinsic fluorescence.

BACKGROUND OF THE INVENTION

It is of course elementary that all microbial cells produce energy for their cellular activity through respiration. As cellular respiration occurs in living cells, pyridine nucleotides are reduced, flavins are oxidized and other coenzymes and metabolites are produced. Alternatively, spores are found to be abundant with a calcium dipicolinic acid complex (a fluorescent compound otherwise rare in nature). The oxidation state of pyridine nucleotides, flavins and other cofactors, and/or the presence of calcium dipicolinate, can be simultaneously elucidated by concurrent excitation of each component with the appropriate electromagnetic radiation followed by detection of the characteristic radiation emitted by these individual fluorophores. Simultaneous frequency-modulated excitation of a sample with multiple energies characteristic of the excitation for fluorescent cellular and endospore components with the subsequent collection and detection of emitted, reflected and scattered light energies (associated with the fluorophores, respectively) is fundamental for the detection of microbes in a sample or on a non-living surface by the method described herein. It will be appreciated by those skilled in the art that the use of frequency-modulated ultraviolet light excites aromatic amino acids and nucleic acids, some of whose emission is self-absorbed by the sample sequentially exciting calcium dipicolinate and pyridine nucleotides, some of whose emission is self-absorbed by the sample in turn exciting cofactors (e.g., flavins), part of whose emission is used to excite porphyrins and other flavins. The fluorescent emissions of the sample are collected and analyzed as described previously.

The detection of respiring cells in real world samples is made more reliable by the aforementioned method for two reasons. First, the simultaneous excitation of microbes by multiple excitation energies and ensuing coincident detection of numerous fluorescence signals reduces the chance of interference, as the probability of an interference source duplicating the characteristics of numerous fluorophores is extremely small. Second, the relative quantities of the intrinsic metabolites, and thus of the resulting fluorescent signals, have been found to fall within defined physiological ranges. This is true also of the sum of the resulting fluorescence signals associated with each excitation wavelength. Analysis of the signals is achieved with a method capable of two things: (1) separating the detected fluorescent signals originating from any microbes present from interferences or background signals and/or scattered excitation signals, and (2) a requirement that the sum of the intensities of the signals from microbial metabolites associated with each excitation frequency for microbial components and spore components fall within physiological ranges. Thus, the basis for the detection of microbes in a sample is comprised of the following steps: first, excitation of a sample simultaneously with multiple frequency-modulated excitation energies characteristic of cellular metabolites, microbial components, and spore components; second, the subsequent collection of the resulting frequency-modulated fluorescence signals; and finally, analysis of the collected signals with a method capable of removing background fluorescence and comparing the relative signal magnitudes of metabolites to known physiological ranges. In the present invention, since each excitation source is frequency modulated the resulting sum of fluorescence signals resulting from that excitation energy is similarly frequency modulated (for frequencies longer than the fluorescence lifetime of the excited intrinsic microbial fluorophore) and can be thus distinguished from any background signals by use of any analysis method capable of detecting only the resultant emission signals occurring at the frequency of the excitation radiation. One example of such an analysis method well known to those skilled in the art would be the use of the discrete Fourier transform on the detected fluorescence signals over a period of time that meets or exceeds the requirements of the Nyquist-Shannon sampling theorem.

Long-established technologies and methods used for microbial detection rely upon detection of products resulting from metabolic reactions, immunological capture or the amplification of expected nucleotide sequences. Since this invention employs detection of multiple intrinsic fluorophores from microbes, coupled with an analysis of the relative amount of signals due to these fluorophores, it can not only determine the presence of microbes, but is also capable of differentiating between viable cells, non-viable cells and spores. This method and apparatus uses no reagents, requires no physical contact with the sample, and delivers 'real-time' results.

There are other microbial detection methods that utilize fluorescence. Many of the flow cytometry methodologies rely on the fluorescence of dye molecules conjugated to immunological proteins targeted to the analyte of interest. An example of this can be found in U.S. Pat. No. 4,745,285 (to Recktenwald, et al.). Other fluorescence methods use added fluorescent metabolic dyes or dye conjugates (as in U.S. Pat. No. 4,900,934 to Peeters, et al.).

Some of the fluorescence-based microbe detection methodologies utilize intrinsic cellular fluorophores. One method (U.S. Pat. No. 5,424,959 to Reyes, et al.) simply compares the fluorescence spectra of the sample with a library of spectra. The method described in U.S. Pat. No. 5,474,910 to Alfano, compares the fluorescence of a sample surface to that of a clean surface. A popular intrinsic fluorophore used in microbial detection methods is the reduced pyridine nucleotide NADH. In U.S. Pat. No. 5,701,012 to Ho, NADH fluorescence is detected in a forced airstream containing the sample and compared to a blank. Alternatively, the ratio of NADH fluorescence to either the scattered excitation signal or other fluorescence emissions is used in U.S. patents to Powers (U.S. Pat. Nos. 5,760,406 and 5,968,766).

In U.S. Pat. Nos. 5,760,406 and 5,968,766, which issued 02 Jun. 1998 and 19 Oct. 1999, respectively, and which are incorporated herein by reference, there is disclosed a method and apparatus for the detection of microbes on non-living surfaces and samples. The sample to be examined is excited with electromagnetic radiation (1) having a wavelength greater than 350 nm causing the excitation of pyridine nucleotides present in microbial cells, and (2) having a wavelength below 340 nm as a measure of other characteristics of the environment. The ratios of the microbial pyridine nucleotide fluorescence emission (resultant from the excitation at the different wavelengths) to the reflected excitation signals are calculated and compared, as the basis for both the detection and quantitation of microbes present on the sample. This invention is able to locate and quantitate microbes on non-living surfaces, including meats.

Whereas the aforementioned patents to Powers depend upon ratio fluorescence for the detection of a single metabolite, the present invention utilizes excitation of one or more fluorophores coupled with an algorithm that subtracts the detected signals due to the scattered/reflected excitation energies. This difference in design and methodology makes the current invention able to detect and quantitate microbes on non-living surfaces, in liquids and in air relative to other fluorescence methods using only one detector that collects all the resulting sample fluorescence over time provided that excitation energies can be effectively optically filtered and thus prevented from reaching the detector.

In U.S. Pat. No. 6,750,006, which issued Jun. 15, 2004, multiple intrinsic fluorescence emission signals resultant from multi-wavelength excitation are used coupled with an algorithm that subtracts the contributions from reflected and scattered excitation energies. The current invention is differs from U.S. Pat. No. 6,750,006 in that the contribution from the background fluorescence is accounted for by the analysis method (like the Fourier transform of the time-dependant signal) and that it can utilize many fewer photodetectors. The present invention shares with U.S. Pat. No. 6,750,006 the benefit of the certain detection of microbes from the detection of multiple intrinsic fluorophores, reducing the probability of false positive results due to background interferences. The detection of microbes with the foregoing method and apparatus will have uses in biowarfare agent detection, cell sorting, medical diagnostics, sterilization verification, water quality testing, food production and preparation safety, and emergency response teams tasked with the detection, decontamination and protection of public infrastructure facilities.

With near constant announcements of bacterial contamination in foodstuffs (meats, poultry, seafood, juices, fruits and vegetables), there has been a need to provide a method and apparatus that can be used to detect such microbial contamination in foods, on foods and on food preparation surfaces. This method and apparatus, as an object of the invention, should be operated inexpensively and rapidly in, for example, meat and poultry production facilities.

It is yet another object of the invention to provide a method and apparatus for use in the detection of microbial contamination on foods in which the fluorescence of pyridine nucleotides, flavins and other cofactors and spore components are excited by electromagnetic radiation to distinguish the metabolic reactions and spore components of microbes from the tissue of foodstuffs, allowing microbial contamination on foods to be determined without contact with said food.

It is accordingly an object of the invention to provide a method and apparatus that can be used in the detection of microbial contamination on non-living surfaces, in liquids and air. As a specific object of the invention, the method and apparatus can be used to find microbes and microbial contamination inexpensively and rapidly in, for example, healthcare facilities, research laboratories, water treatment and testing stations, public buildings and on the battlefield.

It is yet another object of the invention to provide a method and apparatus for use in the detection of microbial contamination on non-living surfaces and in liquid and air samples in which the fluorescence of pyridine nucleotides, flavins and other cofactors and spore components are excited by electromagnetic radiation to distinguish the metabolic reactions of microbes and/or presence of spores from the background of the media or scattering, allowing microbial contamination in samples to be determined without contact with said sample.

It is yet another object of the invention to provide a method and apparatus for use in the differentiation between viable cells, non-viable cells, spores and non-contaminated samples in which the fluorescence of pyridine nucleotides, flavins and other cofactors and spore components are excited by electromagnetic radiation with the differences in the relative quantities of the intrinsic fluorophores in each used to distinguish the presence of microbes from the background of the media or scattering.

SUMMARY OF THE INVENTION

The concepts of the present invention reside in a method and apparatus for the detection of microbes in which samples are exposed to frequency-modulated electromagnetic radiation of numerous specific energies capable of exciting fluorescence from various metabolites, cofactors and cellular and spore components. Thus, the microbial cells and spores to be sampled (and more specifically the excited metabolites, cofactors and/or other cellular, viral and/or spore components) contained therein emit frequency-modulated fluorescence that can be measured. The collected fluorescence signals (associated with the fluorescence emitted from the cellular/viral/spore components) are analyzed with a method capable of (1) removing any background or reflected and scattered excitation signal, and (2) comparing the sum of the relative fluorescent signals of metabolites, cofactors and spore components to known physiological ranges.

Thus, the method and apparatus of the present invention provides an inexpensive and rapid way in which to scan samples to detect and quantitate the presence of microbial contamination without contact with the sample. Being able to evaluate microbial contamination in a sample without contact reduces the risk of introducing contamination.

In accordance with this form of the invention, it is frequently desirable to utilize light source(s) emitting electromagnetic radiation above 200 nm. In accordance with the present form of the invention, the light emitted by the light source is specific to or filtered to pass therethrough electromagnetic radiation of energies specific to excite nucleic acids, aromatic amino acids, pyridine nucleotides, flavins, porphoryns, cofactors and/or calcium dipicolinate.

In accordance with another embodiment of the invention, it is possible, and sometimes desirable, to direct frequency-modulated electromagnetic radiation of ultraviolet energies (wavelengths between 200 and 300 nm) at the sample. The ultraviolet light excites aromatic amino acids and nucleic acids, some of whose emission is self-absorbed by the sample sequentially exciting calcium dipicolinate and pyridine nucleotides, some of whose emission is self-absorbed by the sample in turn exciting cofactors (e.g., flavins), part of whose emission is used to excite porphyrins and other flavins. The fluorescent emissions of the sample are collected and analyzed as described previously. The use of ultraviolet light results in a relatively shallow sampling penetration depth of a sample.

In accordance with another embodiment of the invention, it is possible, and sometimes desirable, to direct frequency-modulated electromagnetic radiation of energies capable of exciting specific metabolites, cofactors and cellular/spore components and also energies that do not interact with the microbes. Thus, in accordance with this embodiment of the invention, the resulting frequency-modulated fluorescent signal emanating from the sample (both from the microbial components and those simply reflected and scattered from the sample) can be measured and the presence of microbes determined by comparing the ratios of the sums of the emitted signals associated with each excitation frequency from the microbes compared to those reflected and scattered from the sample.

In accordance with the practice of the invention, a sensor is used to detect not only the fluorescence generated by the intrinsic fluorophores but also to detect the reflected or scattered electromagnetic radiation. This serves to normalize the signal and compensate for variations in the signal that might otherwise be caused by the use of varying distances between a probe and the sample being scanned and variations between different samples or surfaces.

Most commercially available microbe detectors rely on the growth of microbial cultures to obtain sufficiently large samples (outgrowth) for the subsequent application of differential metabolic tests for species (genus) identification. However, techniques requiring bacterial outgrowth may fail to detect viable but non-culturable cells. Conversely, the growth media employed may favor the growth of bacteria with specific phenotypes.

Other approaches to microbial detection depend upon the immunological capture of either the microbes themselves or their components. The most popular immunoassay method, enzyme-linked immunosorbent assay (ELISA), has a best detection limit of several hundred cells. (This is well below the $ID_{50}$ of extremely infectious bacteria such as *Shigella flexneri.*) These techniques likewise involve significant problems because the antibodies employed are very sensitive to variations in pH, ionic strength and temperature. Antibodies directed to microbial components not only are relatively expensive to develop and produce, but are also susceptible to degradation by a host of proteolytic enzymes in 'dirty' samples. In addition, the density of antibody molecules supported on surfaces (e.g., microwell plates or magnetic beads) is not as high as is frequently necessary.

More sensitive but less rapid typing schemes utilize the polymerase chain reaction (PCR) for amplification of bacterial DNA or RNA, followed by nucleic acid sequencing to detect the presence of a particular bacterial species. Such general amplification and sequencing techniques require technical expertise and are not easily adaptable outside of specialized laboratory conditions. PCR-based techniques utilize the inference of microbial presence, since these techniques provide only a positive analysis for an intact target nucleic acid sequences, not necessarily microbes. Moreover, the detection of specific microorganisms in environmental samples is made difficult by the presence of materials that interfere with the effectual amplification of target DNA in 'dirty' or real-world samples.

Mass spectral analysis of volatile cell components (e.g., fatty acids) after sample lysis or pyrolysis has been used for the detection of bacteria and viruses. Unfortunately, identification of the analyte is unreliable as the compositions of a microbe's volatile components change depending upon different environmental growth conditions.

Immunological, mass spectral and PCR-based methods are all unable to ascertain if microbes in the sample were viable. Immunological and PCR-based methods both use relatively expensive reagents that require special handling. The microbial detection method and apparatus described herein is able to determine the viability of detected bacteria, fungi, protozoa, and rickettsiae. The method and apparatus requires no reagents, no contact with the sample, inexpensive to perform and delivers 'real-time' results. These, and other objects, features and advantages of the present invention will become apparent upon review of the following detailed descriptions of the disclosed embodiments and the appended claims.

DETAILED DESCRIPTION OF THE INVENTION

The practice of the invention requires the use of frequency-modulated electromagnetic energies capable of exciting biological material which is intrinsically fluorescent, where electromagnetic radiation is directed from the light source towards the sample, passing through the excitation filters and focusing optics if necessary, to excite the intrinsic fluorophores in the sample. The resulting fluorescence will also be frequency-modulated, with the frequency modulation of said fluorescence emissions being modulated at the same frequency at which it was excited. Using methods known to those skilled in the art, it is possible to separate the resulting contribution to the measured signal at each frequency due to microbial intrinsic fluorescence. Since the relative amount of fluorescent metabolites are coupled in viable (living) cells by cellular chemical reactions (e.g., glycolysis, oxidative phosphorylation, etc.), the relative signal strengths of the background-corrected metabolite fluorescence retain these relationships. A similar situation exists for cells that are nonviable (dead); as metabolic reactions in the dead cell begin to uncouple upon degradation of physiological structures in the cell, certain pools of oxidized fluorescent metabolites build up relative to others. (Spores contain unique and rare fluorescent components that can be used for detection.) Use of the relative amounts of the resulting fluorescence signals can be used to differentiate between the physiological status of microorganisms and their relative overall signal strengths be used to quantitate the number of microorganisms present in a sample. The contributions to the overall detected signal of scattering and reflected excitation energies from each of the frequency-modulated excitation sources can be determined by measuring the overall detected signal associated with each excitation source separately with and without known samples. As the sample will be continuously excited with frequency-modulated radiation, the background fluorescence of the sample will be compensated for with the methods used to separate the resulting contribution to the measured signal at each frequency due to microbial intrinsic fluorescence.

Figure 1:
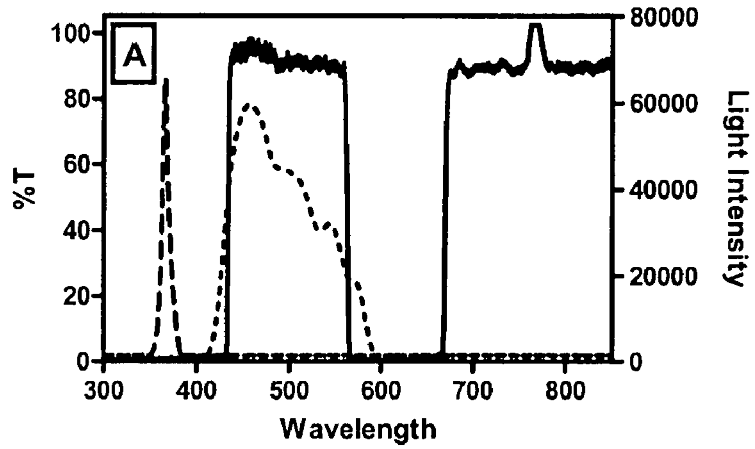
FIG. 1 shows the spectrum of excitation sources (dashed line), the resulting emission spectra from a solution of bacteria (*Bacillus thuringiensis,* dotted line) and the transmission spectrum of a multi-notch filter designed to block excitation energy from the photodetector but allow emission energy to reach said photodetector (solid line). The excitation source and emission spectra are shown for excitation sources of 365 nm (A), 590 nm (B) and 635 nm (C).
Figure 1:
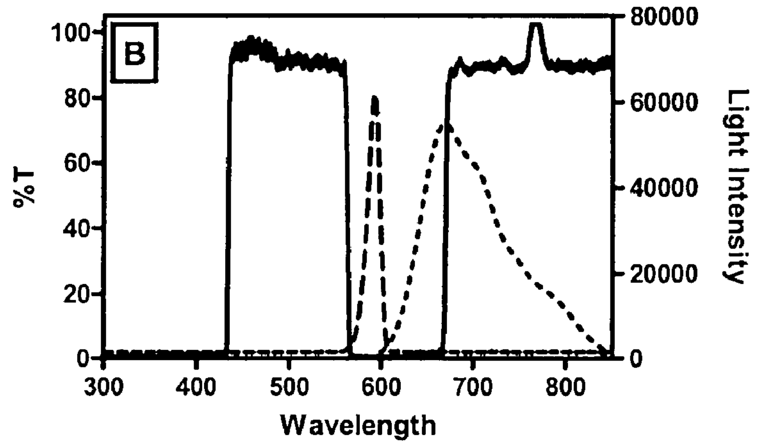
Figure 1:
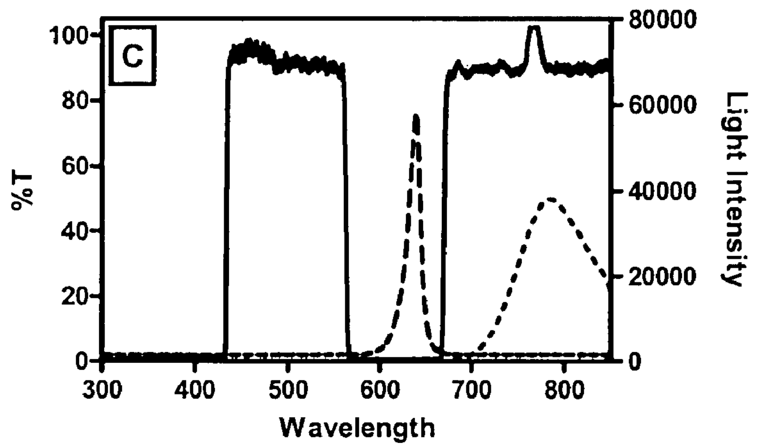

The optical filter designed to block excitation energy from the photodetector but allow emission energy to reach said photodetector is shown as the solid line in FIG. 1. It will be appreciated by one skilled in the art that the use of a multi-notch filter with this design can be used to prevent much of the excitation energy (dashed lines) from reaching the detector used to detect fluorescent signal intensities (dotted line).

The collected emission energies associated with each frequency-modulated excitation source, having been converted to amplified electrical signals, are analyzed with a method capable of removing any background fluorescence and scattered excitation contributions. The choice of excitation and emission energies used in a specific embodiment depends upon the target microbes and their expected physiological status. Table I lists the excitation and emission ranges of some of the more abundant intrinsic fluorescent compounds found in various microbes (and proteinaceous toxins) and indicates their likely presence in each. (Proteinaceous microbial toxins can be detected using this method and apparatus in a manner similar to that used for the detection of viruses.)

practice of the invention, the detection method requires the relative ratios of the detected and background-corrected signals to lie within certain physiological ranges.

Figure 4:
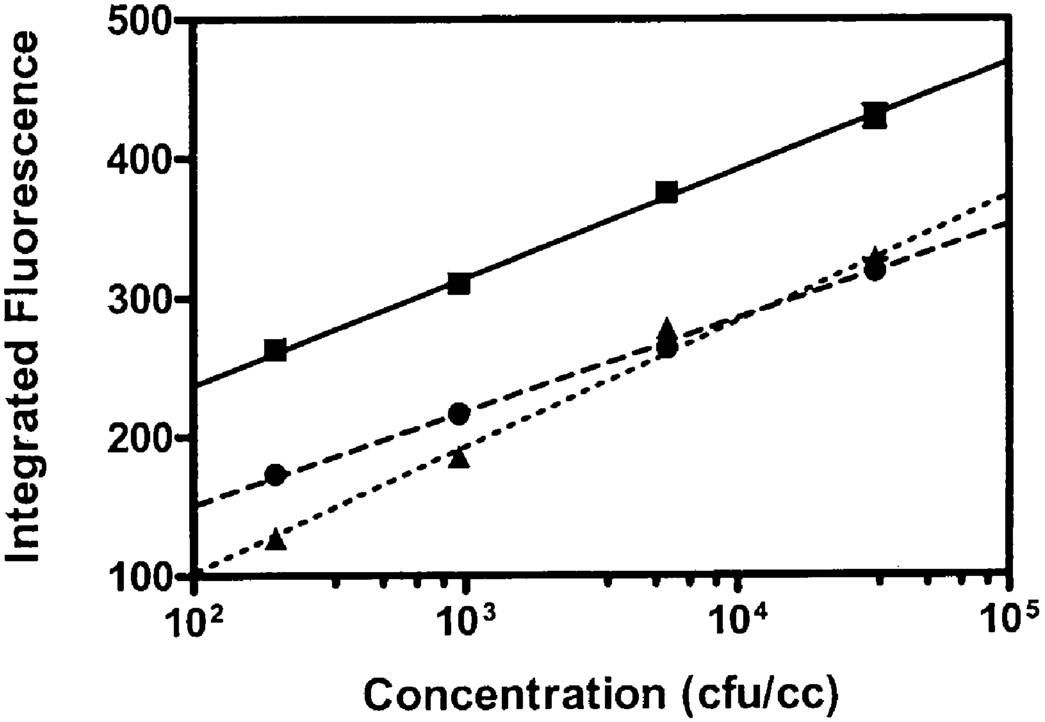
FIG. 4 shows the response of the integrated reduced pyridine nucleotide (RPN) fluorescence emission (365 nm excitation) to concentration of a mixture of *Bacillus thuringiensis* cells and spores in water.

FIG. 4 shows the response of the integrated reduced pyridine nucleotide (RPN) fluorescence emission (365 nm excitation) to concentration of a mixture of *Bacillus thuringiensis* live cells and spores in water. This shows that the amount of intrinsically fluorescent biological material can be determined from the total frequency-associated strength.

The embodiments of the present invention described above are intended to be merely exemplary, with other configurations, variations and modifications utilizing the fore mentioned basic ideas available to those skilled in the art without departing from the spirit of the invention. The scope of this method and apparatus to detect microbes includes utilization of simultaneous excitation of multiple intrinsic microbial fluorophores with subsequent analysis of the detected emissions with methods that concurrently account for background signals and require said signals to lie within physiological ranges. All variations, modifications and configurations are intended to be within the scope of the present invention as defined in the appended claims.

TABLE I

Excitation and Emission Ranges for Microbial Fluorophores.

| Excitation Range | Emission Range | Fluorophore | Viable Cells | Non-viable | Spores | Viruses | Toxins |
|---|---|---|---|---|---|---|---|
| 260-285 | 340-360 | Nucleic Acids | X | X | X | X | |
| 265-280 | 340-360 | Tryptophan | X | X | X | X | X |
| 265-280 | 340-360 | Tyrosine | X | X | X | X | X |
| 270-280 | 380-400 | ATP | X | | | | |
| 270-290 | 460-480 | Ca-Dipic | | | X | | |
| 310-330 | 400-430 | Ca-Dipic | | | X | | |
| 320-330 | 430-450 | RPN | X | | | | |
| 340-365 | 430-450 | RPN | X | | | | |
| 340-360 | 470-490 | RPN | X | | | | |
| 430-450 | 520-535 | Flavins | X | | | | |
| 470-485 | 560-580 | Flavins | X | | | | |
| 560-585 | 615-680 | Porphyrins | X | X | | | |
| 560-580 | 620-700 | Flavins | X | X | | | |
| 610-670 | 750-800 | Ca-PDCA | | X | X | | |
| 650-670 | 730-780 | Unknown | | X | X | | |

(In Table I, ATP is adenosine triphosphate and RPN refers to the reduced pyridine nucleotides. PDCA refers to pyridine dicarboxylic acids.)

Figure 2:
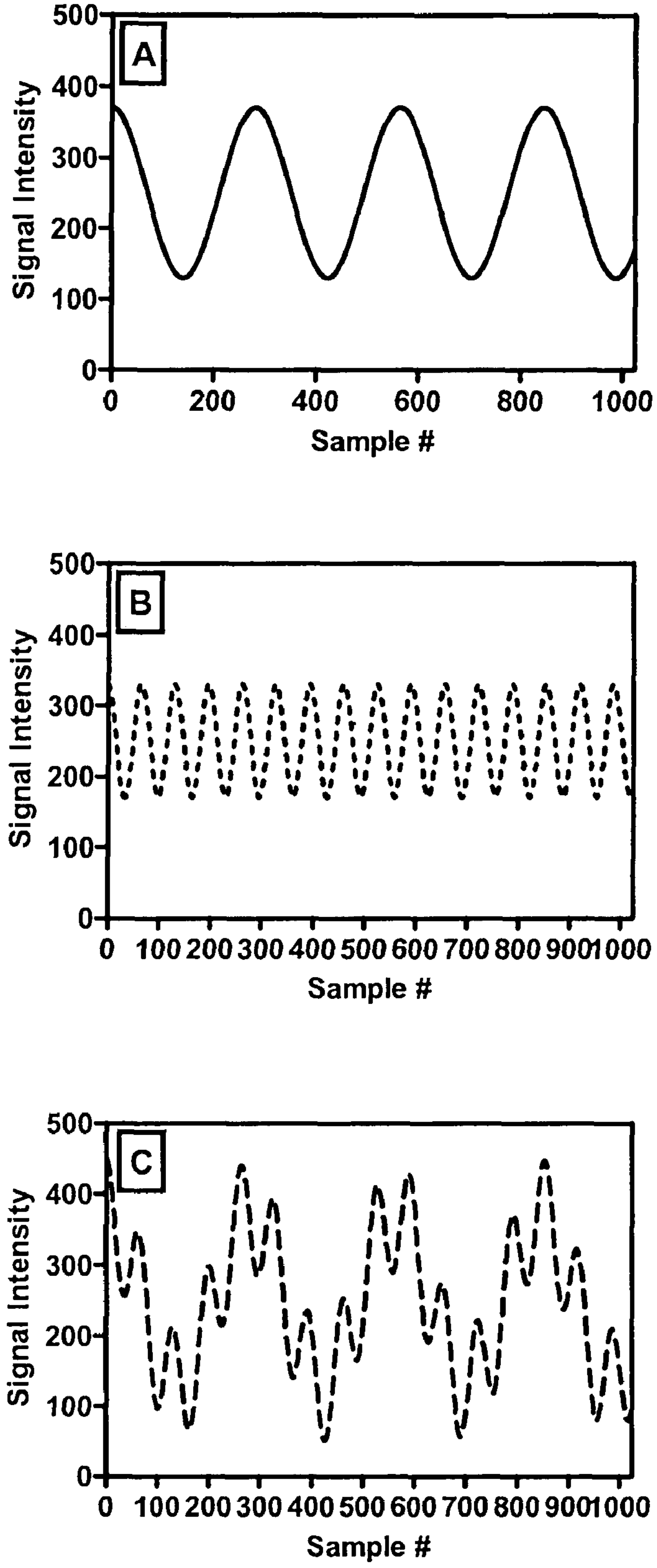
FIG. 2 shows the sinusoidal lower frequency modulation of an excitation source (A), another higher frequency modulation of another excitation source (B), and the total resultant fluorescence signal (C).

FIG. 2 shows a sinusoidal lower frequency-modulation of an excitation source (A), another higher frequency-modulation of another excitation source (B), and the total resultant fluorescence signal (C). Separation of the total resulting fluorescence signal associated with each excitation frequency can be accomplished electronically with filtering circuitry, mathematically with a method capable of calculating the intensity of each frequency-modulated signal (including, but not limited to, a discrete Fourier transform), or both.

Figure 3:
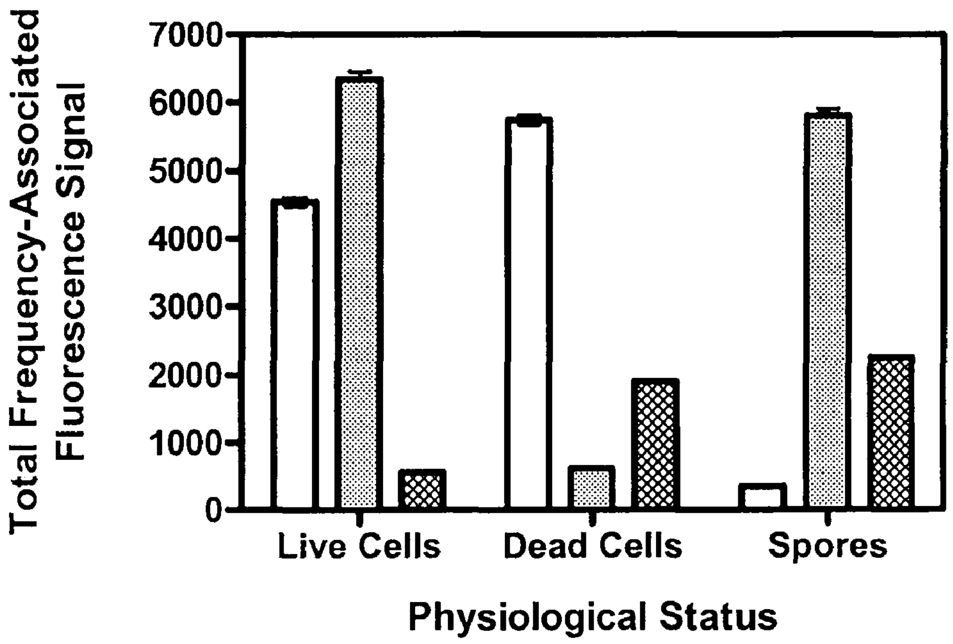
FIG. 3 shows the total fluorescence signals from live, dead and sporulated bacteria (*Bacillus thuringiensis*) associated with the 365 nm (clear bars), 590 nm (shaded bars) and 635 nm (hatched bars) excitation energies, respectively.

FIG. 3 shows the total fluorescence signals from live, dead and sporulated bacteria (*Bacillus thuringiensis*) associated with the reduced pyridine nucleotide fluorescence (365 nm excitation, clear bars), flavins and/or hemoproteins (590 nm excitation, shaded bars) and 635 nm (hatched bars) excitation energies, respectively. As the different physiological states of bacteria exhibit different emission intensities, the differences between the relative amounts of emission signals associated with each excitation energy can be used to determine the physiological status of the detected microorganism. In the

What is claimed:

1. A method for the detection and enumeration of microbes comprising:

a. exciting multiple intrinsic microbial fluorophores having a specific range of electromagnetic radiation wavelength above 200 nm with frequency-modulated electromagnetic radiation; whereby any microbes present containing intrinsic fluorophores are excited to emit fluorescence, some of whose fluorescence is self-absorbed to excite other microbial fluorophores that in turn emit fluorescence and whereby said microbe containing intrinsic fluorophores is excited to emit fluorescence at that frequency, and;

b. detecting the fluorescence signal resulting from the frequency-modulated excitation, and c. separating the resulting contribution to the measured signal at each excitation frequency due to microbial intrinsic fluorescence with a method capable of calculating the intensity of each frequency-modulated signal, and;

d. determining that the ratios of the total detected fluorescence signals associated with each excitation frequency lie within expected physiological ranges, thereby determining the number of microbes by the magnitude of the integrated fluorescence signal associated with an excitation frequency where the total detected fluorescence signals associated with each excitation frequency lies within an expected physiological range.

2. A method as set forth in claim 1, wherein said intrinsic microbial fluorophores are selected from the group consisting of nucleic acid polymers, tryptophan-containing proteins, tyrosine-containing proteins, adenosine triphosphate, calcium dipicinolate, reduced pyridine nucleotides, flavins, porphyrin-containing proteins, alkaline earth metal salts of pyridine dicarboxylic acids, and other components excited in the 610-670 nm region.

3. The method of claim 1 wherein the microbes to be detected include bacteria, fungi, protozoa, and rickettsiae; and the intrinsic microbial fluorophores used to detect the microbes include nucleic acid polymers, tyrosine-containing proteins, tryptophan-containing proteins, adenosine triphosphate, reduced pyridine nucleotides, flavins, porphyrin-containing proteins, alkaline earth metal salts of pyridine dicarboxylic acids, and others excited in the 610-670 nm region.

* * * * *